Figure 1:
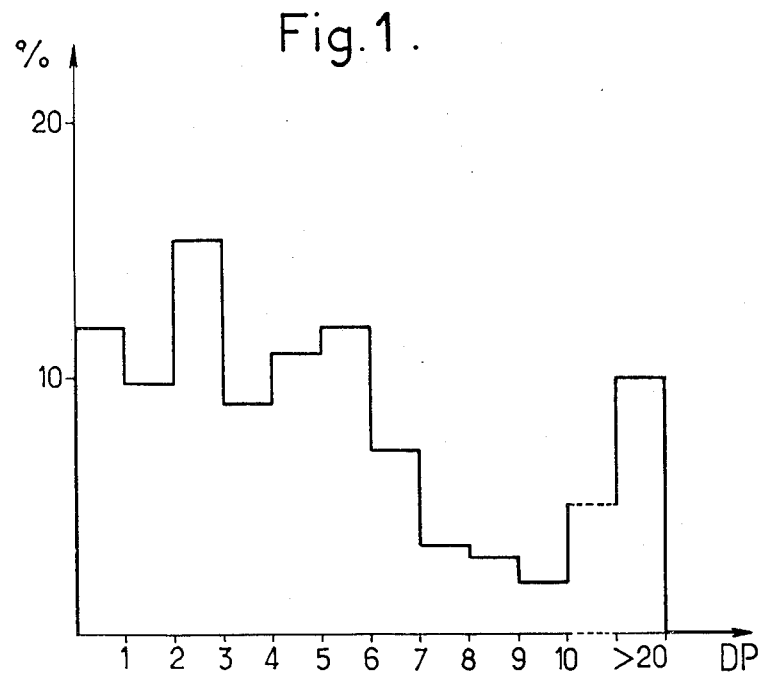

United States Patent [19]
Verwaerde et al.

[11] 4,445,938
[45] May 1, 1984

[54] HYDROGENATED STARCH HYDROLYSATE

[75] Inventors: Françoise Verwaerde, Lambersart; Serge Gosset, Lestrem; Michel Huchette, Merville, all of France

[73] Assignee: Roquette Freres, Lestrem, France

[21] Appl. No.: 340,222

[22] Filed: Jan. 18, 1982

Related U.S. Application Data

[63] Continuation of Ser. No. 109,066, Jan. 2, 1980, abandoned.

[30] Foreign Application Priority Data

Jan. 8, 1979 [FR] France ............................ 79 00370

[51] Int. Cl.$^3$ .................. C13K 1/06; C07G 3/00; C08B 31/00; C12N 9/28
[52] U.S. Cl. ............................ 127/29; 127/38; 435/42; 435/96; 435/99; 536/1.1; 568/863
[58] Field of Search ............... 127/29, 38; 435/42, 435/96, 99; 568/863; 536/1.1

[56] References Cited

U.S. PATENT DOCUMENTS

| | | | |
|---|---|---|---|
| 3,285,776 | 11/1966 | Scallet | 435/96 X |
| 3,535,123 | 10/1970 | Heady | |
| 3,804,716 | 4/1974 | Langlois | |
| 3,838,006 | 9/1974 | Hijiyd | 435/96 X |
| 3,897,305 | 7/1975 | Hurst | 435/96 |
| 3,922,196 | 11/1975 | Leach | 127/29 X |
| 3,922,198 | 11/1975 | Kuske | 435/96 |
| 3,922,200 | 11/1975 | Walon | 435/96 |
| 4,113,509 | 9/1978 | Leach | 435/96 X |

FOREIGN PATENT DOCUMENTS

| | | |
|---|---|---|
| 861195 | 2/1961 | United Kingdom . |
| 1037254 | 7/1966 | United Kingdom . |
| 1426997 | 3/1976 | United Kingdom . |
| 1470325 | 4/1977 | United Kingdom . |
| 1477587 | 6/1977 | United Kingdom . |
| 2001075 | 1/1979 | United Kingdom . |

*Primary Examiner*—Sidney Marantz
*Attorney, Agent, or Firm*—Larson and Taylor

[57] ABSTRACT

This invention relates to a starch hydrolysate which can be optionally hydrogenated as well as the process for preparing said hydrolysate and uses thereof.

Its glucidic spectrum corresponds to:

a content of monosaccharides (DP=1) less than 14%, a content of disaccharides (DP=2) less than 35%, preferably less than 20%, a content of oligosaccharides of DP 4 to DP 10 ranging from 42% to 70%, preferably from 42 to 60%, the oligosaccharides of DP 5 to DP 7 representing by themselves a proportion preferably higher than 25% and more preferably higher than 30%, a content of polysaccharides of DP higher than 10, less than 32%, and preferably less than 25%.

The hydrolysate is useful in the preparation notably of human foodstuff.

14 Claims, 2 Drawing Figures

HYDROGENATED STARCH HYDROLYSATE

This is a continuation of application Ser. No. 109,066, filed Jan. 2, 1980, now abandoned.

The invention relates to a starch hydrolysate, possibly hydrogenated.

It also relates to the process for preparing this hydrolysate as well as the uses thereon.

It is a particular object of the invention to providing a hydrolysate which is not too viscous, which is stable in solution, which has good nutrient and physiological qualities, good physical properties, good anticrystallizing power, and which, if necessary, is not cariogenic.

Now, applicant has found that hydrolysates responding to this group of properties had to be neither too rich in polysaccharides of high molecular weight, nor too rich in saccharides of low molecular weight, the glucid spectrum having, on the contrary, to show a relatively high content of oligosaccharides, it being understood that the saccharides, oligosaccharides and polysaccharides concerned are present possibly in the form of the corresponding hydrogenated products.

Consequently, the starch hydrolysates, possibly hydrogenated, which are the subject matter of the invention, have from a very general point of view, a relatively high content of oligosaccharides simultaneously with a comparatively low content of saccharides and of polysaccharides, and they comprise linear or branched chains.

Thus, the above-said optionally hydrogenated hydrolysates have a relatively high content of oligosaccharides of DP 4 to DP 10, preferably from DP 5 to DP 7 (DP=degree of polymerisation) and a comparatively low amount of mono- and di-saccharides as well as of polysaccharides with a DP higher than 10, those of these hydrolysates which are non-cariogenic being in hydrogenated form and having a very low content of polyols of DP higher than 20, this content being advantageously less than 3% and, preferably, less than 1.5%.

The optionally hydrogenated hydrolysates according to the invention are characterized by a glucid spectrum corresponding to:

a content of monosaccharrides (DP=1) less than 14%.
a content of disaccharides (DP=2) less than 35%, preferably less than 20%,
a content of oligosaccharides of DP 4 to DP 10 ranging from 42% to 70%, the oligosaccharides of DP 5 to DP 7 representing by themselves a proportion preferably higher than 25%, and more preferably higher than 30%.
a content of polysaccharides of DP higher than 10 less than 32%, preferably less than 25%.

The hydrogenated hydrolysates corresponding to the above-said glucid spectrum and which, in addition, are devoid of cariogenic character, have, besides, a content below 3%, preferably below 1.5%, of polyols of DP higher than 20.

The percentages which have just been discussed are percentages by weight, expressed on the dry matter of hydrolysates.

The hydrolysates according to the invention with a particularly advantageous glucid spectrum will be described below.

Figure 2:
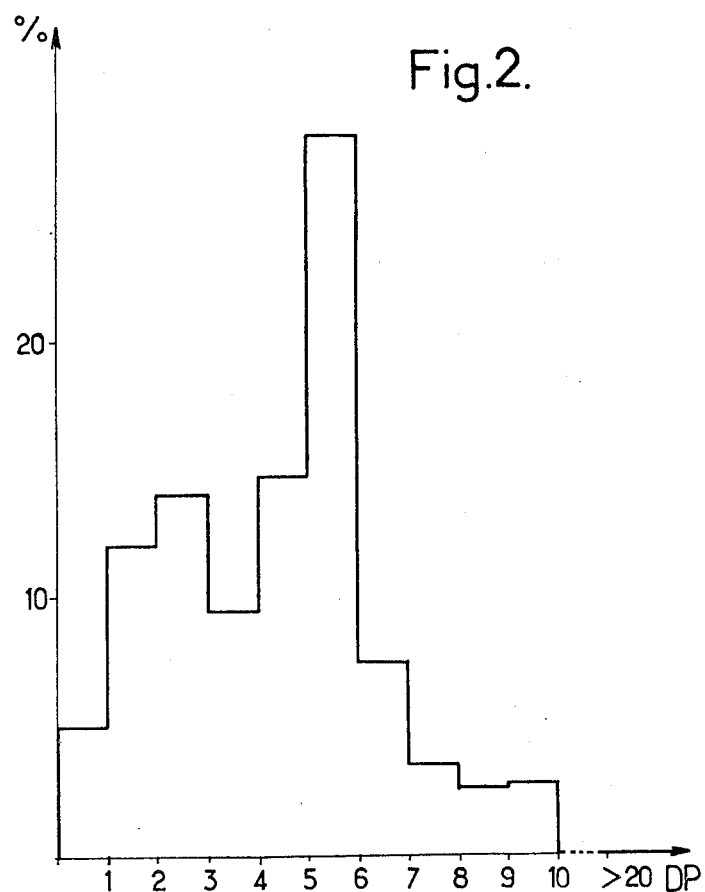

FIGS. 1 and 2 are graphs showing the glucidic distribution of respectively the hydrolysates given in Example 2, table II and Example 3, table VI.

Applicant has found that, for numerous applications, both in the industrial field and in the food field, dietetics or pharmaceutical field, there was obvious interest in having available a starch hydrolysate with a well defined composition, and in particular with a relatively high content of oligosaccharides of DP 4 to DP 10. Too large an amount of saccharides with low molecular weight or of polysaccharides can in fact show, for very precise applications, a good many drawbacks.

Applicant has observed that an increase in the proportion of high molecular weight polysaccharides (DP higher than 10) accounts for an increase in the viscosity of the hydrolysates and especially in a lack of stability in solution (retrogradation) of the latter.

Thus, it has observed more particularly that syneresis phenomena, appearing on storage for long periods (several weeks) of the mixtures used for the preparation of foundry moulds and cores (silicates+borax+hydrogenated glucose syrups) and which are manifested by heterogeneities within the mixture, were due especially to the presence of polyols of high DP.

These same phenomena occur on storage of the syrups alone, whether or not hydrogenated, which presents drawbacks for certain applications such as the use of the hydrolysates concerned in foodstuff for patients. In this application, besides the absence of retrogradation on storage, a quick absorption of carbon hydrates is sought, and thus the content of high molecular products, considered as being slowly assimilated, is to be limited.

Applicant has also shown that the very high molecular weight products (DP higher than 20) which are present in hydrogenated syrups are essentially responsible for the acidification which is produced by the bacteria of the mouth, which acidification causes attack on the dental enamel. Such hydrogenated hydrolysate used in confectionery, and, in particular, in hard candies must not contain polyols with a DP higher than 20, or at the most, an amount less than 3% to preserve the non-cariogenic character.

The low molecular weight saccharides constitute products which are more easily assimilable, from the nutritional point of view, but they possess a high sweetening power, a strong osmolality and can account for certain intestinal disorders. Their presence in too large an amount is consequently not wanted, in some products intended for patient foodstuff, where a light sweet taste, a weaker osmolality and a good physiological tolerance of products is sought. In some applications, such as the manufacture of foundry moulds or cores, the presence of mono- and di-saccharides in too large an amount reduces the physiological qualities aimed at (compressive strength). Thus, a hydrogenated glucose syrup used in foundry, as a breakdown agent, must contain a quantity of sorbitol (DP 1), sufficient to ensure the control of the water content of the medium in which the syrup is used, without this amount reaching the values liable to cause a reduction in the physical properties; for example, too much sorbitol and/or also too much maltitol (DP 2) would cause too sudden a change in the mixture silicate-syrup on casting (breakage of the mould or core).

In confectionery, in the preparation of hard candies, the starch hydrolysates with a high content of products of DP 1 and DP 2 are difficult to handle. The hard candies are not stable on storage, because of too high a hygroscopy.

Taking the foregoing into account, the uses according to the invention, of the above-said hydrolysates are situated in various fields according to the glucid spectrum.

These uses comprise:
preparation of binders for foundry moulds and cores;
human feeding notably manufacture of jams, chocolates, sausages, ice-creams, chewing-gums and hard candies, the food concerned being not cariogenic when these hydrolysates are hydrogenated and when their content of product of DP higher than 20 is less than 3%;
infant dietetics and feeding of patients;
preparation of polyurethanes and
constitution of blood plasma substitutes.

The process according to the invention for preparing hydrolysates, according to the invention, whose content of products of DP 4 to DP 10 is from 42% to about 55% and whose content of products of DP 1 is less than about 5% comprises the action on a previously gelatinized or liquefied starch, preferably by enzymatic action (DE less than 20) of α-amylase, this enzyme being applied in the proportion of 3000 to 20000 I.U./kg d.m. for 8 to 48 hours.

The process according to the invention for preparing hydrolysates, according to the invention, with a content of products of DP 4 to DP 10 ranging from 42% to about 50% and with a relatively high content of about 5 to 14% of products of DP 1, in which process α-amylase and 1,4-amyloglucosidase are made to act simultaneously, is characterized by the fact that said α-amylase and 1,4-amyloglucosidase are applied to a starch previously liquefied by the acid or enzymatic route to a D.E. of 25 at the most, in the proportion of 500 to 4000 I.U./kg d.m. as regards the first and in the proportion of 30 to 500 I.U./kg d.m. as regards the second, the action being continued for 10 to 48 hours until the production of a D.E. of 30 to 40.

The process according to the invention for preparing hydrolysates with a content of oligosaccharides of DP 4 to 10 higher than about 55% and with a content less than 1.5% of products of DP higher than 20 and/or with a content as low as desired, of products of DP less than 4, is characterized by the fact that a hydrolysate of D.E. close to 30 obtained by acid or enzymatic liquefaction of a starch is fractionated by molecular sieving, for instance by elution on a cationic resin, the first fractions which contain the products of high DP and/or the last fractions containing the products of DP less than 4, being eliminated.

To obtain the corresponding hydrogenated products, the hydrolysates obtained at the end of the above-defined process are subjected to conventional hydrogenation, notably by the Raney nickel method.

It is possible to transform these hydrolysates into powder form by resorting to conventional methods such as spraying.

It is possible to use as a raw material for the manufacture of the above-said hydrolysates, modified or unmodified starches from any source such as root starches, corn starches, waxy-maize, starches from wheat, from manioc and the like.

The foregoing considerations are illustrated by the examples which relate to preferred embodiments.

EXAMPLE I

A suspension of starch with 35% of dry matter and with pH 6 is liquefied conventionally by means of a thermoresistant α-amylase of the type Bacillus Licheniformis, by passage at 106° C. for 3 minutes, then is maintained at 95° C. until a D.E. of 16 is obtained. The enzyme is then inhibited by a quick passage at a temperature of 160° C. It is cooled to 60° C. and 100 liters of this hydrolysate is incubated for 30 hours with 8000 I.U. of α-amylase of the Bacillus Subtilis type. The D.E. which is obtained is then 28.0.

The glucidic distribution of the thus obtained hydrolysate is summarized in Table I.

TABLE I

| Products of | % by weight |
|---|---|
| DP 1 | 2.0 |
| DP 2 | 8.0 |
| DP 3 | 12.0 |
| DP 4 | 6.8 |
| DP 5 | 11.6 |
| DP 6 | 20.2 |
| DP 7 | 5.2 |
| DP 8 | 1.8 |
| DP 9 | 2.1 |
| DP 10 | 2.3 |
| between DP 10 and DP 20 | 9.0 |
| DP higher than 20 | 19.0 |

The hydrolysate is purified by successive passages over activated charcoal, anionic and cationic resin. After a concentration of 62,5% (weight/volume), the solution is stabilized by addition of 0,1% of sorbic acid. The osmolality of this product is 450 millios mole/kg.

Different samples of the solution were done and placed respectively at 4° C. and 50° C. for a period of four weeks.

No turbidity is observed on any of the samples. This hydrolysate was administered orally to several patients. Their impression was judged as being very in favour of the product, both as regards its taste and tolerance, secondary effects such as nausea and diarrhoea being absent. Other tests were carried out, by perfusion of the hydrosylate into the jejunum.

It was proved that the hydrolysate releases glucose in the blood at speed as high as the glucose itself.

At the same time, these experiments have proven that the luminal concentration of glucose released by the hydrolysate remained low, thus limiting the risk of diarrhoea.

EXAMPLE 2

A suspension of starch is liquefied by means of hydrochloric acid conventionally to a D.E. of 19.0. After adjustment of the dry matter content to 35% and of the pH to 5.2, to 100 l of the syrup is added at the same time 1900 I.U. of α-amylase and 75 I.U. of amylo 1-4 glucosidase per kg of dry starch. It is incubated at 60° C. The enzymatic reaction is stopped by bringing the substrate rapidly to a high temperature as soon as the D.E. reaches 34, that is to say after 20 hours.

The glucid distribution of this syrup is summarized in Table II.

TABLE II

| Products of | % by weight |
|---|---|
| DP 1 | 12.2 |
| DP 2 | 9.8 |
| DP 3 | 15.4 |
| DP 4 | 9.0 |
| DP 5 | 11.0 |
| DP 6 | 11.7 |
| DP 7 | 7.0 |
| DP 8 | 3.4 |
| DP 9 | 3.0 |

TABLE II-continued

| Products of | % by weight |
|---|---|
| DP 10 | 2.0 |
| between DP 10 and DP 20 | 5.3 |
| DP higher than 20 | 10.2 |

This glucid distribution is shown in FIG. 1.

The preponderance according to the invention of products of DP 4 to DP 10 is clearly apparent therein.

After filtration and purification, the syrup is hydrogenated.

The preparation of three mixtures called products A, B and C and constituted in the following manner was then undertaken:

a pre-mixture containing 1000 grams of a syrup of hydrogenated glucose (identified below and different for each of the products A, B and C) brought previously to 71% of dry matter, 67 grams of anhydrous borax and 90 grams of water, was made up. This pre-mix was then added in the proportion of 20% by weight to a sodium silicate used currently in the foundry industry, of $SiO_2$ modulus equal to 2.4 and having a dry matter content $Na_2O$ of about 55%.

As regards product A, the hydrogenated glucose syrup is constituted by the above-said product of the invention and has a D.E. before hydrogenation of 34.

As regards product B, the glucose syrup is constituted by a hydrogenated glucose syrup of the prior art having a D.E. before hydrogenation of 33 and containing 25% of maltitol.

As regards product C, the glucose syrup is constituted from a hydrogenated glucose syrup of the prior art having a basic D.E. of 55 and containing 50% of maltitol.

The hydrogenated hydrolysates which enter into the composition of the three products A, B and C which will be used in the foundry tests have the glucid distributions which are reported in Table III.

TABLE III

| Products of | Product A | Product B | Product C |
|---|---|---|---|
| DP 1 | 12.2 | 5.2 | 7.5 |
| DP 2 | 9.8 | 24.0 | 52.0 |
| DP 3 | 15.4 | 17.1 | 17.5 |
| DP 4 to DP 10 | 47.1 | 30.0 | 15.5 |
| DP 5 to DP 7 | 29.7 | 11.5 | 7.4 |
| between DP 10 and DP 20 | 5.3 | 4.5 | 6.5 |
| DP higher than 20 | 10.2 | 19.2 | 1.0 |

The preparations A, B and C obtained are kept on a water-bath at 40° C. for 24 hours; this constitutes an accelerated ageing test.

The viscosity was then measured and it was verified whether syneresis existed. The results were:

|  | Product A | Product B | Product C |
|---|---|---|---|
| Viscosity | 1780 | 2300 | 1200 cp |
| Syneresis | no | yes | no |

It appears that the hydrolysate of the invention, whilst having a low basic D.E., does not give rise to prejudicial syneresis, whilst having a lower viscosity more suitable for use in the field of preparing foundry moulds and cores.

The products A, B and C were then used for the fabrication of specimens i.e. test-pieces using a sand for foundry works. The sand and the various products were mixed on a planetary Hobart type apparatus, in the proportion of 3.5% of product with respect to the sand.

On a GF raming apparatus (type SPRA of the STOKVIS Company) samples of 163 g, of 50.8 mm height and a 50 mm diameter, were formed.

Six sets of three specimens were prepared respectively from products A, B and C. A controlled flow of carbon dioxide gas was passed through the mass of these specimens (25° C.–5.5 l/mn at a pressure of 350 g/cm2). The blowing times tested were 5, 10, 20, 30, 60 and 120 seconds.

When the blowing was finished, a shearing force was applied on an INSTRON apparatus (an apparatus marketed by INSTRON limited Co., of England) machine 1122.

The results of the measurements are assembled in Table IV.

TABLE IV

| Specimens based on | Shearing force in g-cm$^2$ after various blowing times | | | | | |
|---|---|---|---|---|---|---|
|  | 5 s | 10 s | 20 s | 30 s | 60 s | 120 s |
| Product A | 2400 | 3900 | 5800 | 6400 | 7500 | 8800 |
| Product B | 1500 | 3750 | 5200 | 6100 | 7600 | 8500 |
| Product C | 1300 | 2750 | 4500 | 5500 | 7000 | 7600 |

On examining these results, it is observed that due to the use of the hydrolysate according to the invention (Product A) the physical characteristics of the corresponding test-piece are higher than the physical characteristics of the test-pieces comprising the hydrolysates of the prior art (Products B and C).

Another series of test specimens was subjected to a carbon dioxide blow for 5 seconds under the previously defined conditions. They were then stored (temperature of 20±1° C. and relative humidity of 65%) for varying times and subjected to shearing forces on the GF apparatus.

The results of the measurements are collected in Table V.

TABLE V

| Test specimens based on | Shearing force in g-cm$^2$ after various storage times | | | |
|---|---|---|---|---|
|  | 1 h | 2 h | 6 h | 24 h |
| Product A | 6100 | 6800 | 8800 | 15000 |
| Product B | 6100 | 6600 | 8300 | 15600 |
| Product C | 2600 | 5050 | 7000 | 12800 |

These measurements confirmed the preceding series. Without syneresis, the product A preserves a performance level equal to that of the product B.

EXAMPLE III

A suspension of potato starch with 35% of dry matter is liquefied conventionally by α-amylase to a DE of 27.0.

This hydrolysate is passed over a column containing 400 cubic centimeters of LEVATIT Ca 9220 brand resin (cationic type resin) placed in the calcium form and this in the proportion of 150 cm3/hour and at 80° C.

The first eluted fractions contain the polysaccharides of very high molecular weight. They are separated from the syrup and represent about 30% by weight of the starting syrup. The hydrolysate no longer containing higher polysaccharides has the composition indicated in Table VI.

TABLE VI

| Products of | % by weight |
| --- | --- |
| DP 1 | 5.0 |
| DP 2 | 12.0 |
| DP 3 | 14.0 |
| DP 4 | 10.0 |
| DP 5 | 14.7 |
| DP 6 | 28.0 |
| DP 7 | 7.5 |
| DP 8 | 3.5 |
| DP 9 | 2.6 |
| DP 10 | 2.7 |
| DP higher than 10 | nil |

This glucidic distribution is represented by the graph of FIG. 2. The preponderance according to the invention of the product of DP 4 to DP 10 is clearly apparent.

After concentration to 50% of dry matter, this hydrolysate is hydrogenated. The syrup obtained can be perfectly suitable for the manufacture of sweets. In order to do this, 1% of citric acid and 0.25% (on dry matter) of saccharin are added to the syrup and the mixture is preheated to 95% before it is passed in a continuous vacuum cooker of the Hamac Hansella type. The product is allowed to cool on a refrigerated surface at 80° C.

The plastic mass thus obtained is placed in a rolling mill shaped into a ribbon, moulded and cut up. The sweets thus obtained are wrapped immediately after cooling They are hard brittle and have an excellent taste. In addition, they have the advantage of being non-cariogenic due to the absence of polyols of DP higher than 20 and the syrup.

The above said hydrogenated syrup has been used for the manufacture of chewing-gum as a constituent of a liquid phase.

In order to do so, 20 parts by weight of basic gum (such as the marketed under the name "Firm Paloja" by L. A. Dreyfus Company) softened to 75° C., are kneaded with 15 parts by weight of hydrogenated syrup to 75% of dry matter, the sweetening power of which was increased by addition of 0.15% on dry matter of saccharin. The solid phase constituted by 52% of powder of sorbitol and 8% of powder maltitol is progressively added and the kneading is carried on for 30 minutes. The chewing-gum thus obtained is non-cariogenic, did not have recrystallization at the surface, they are not sensitive to variations in hygrometry and in temperature of the atmosphere in which they were stored and have an excellent taste.

As result of which and whatever the embodiments adopted, there is thus provided by the invention a starch hydrolysate whose characteristics emerge clearly from the foregoing.

As is self evident and as emerges from the foregoing, the invention is in no way limited to those of its types of application and embodiments which have been more particularly described; it encompasses, on the contrary, all modifications.

We claim:

1. Hydrogenated starch hydrolysate characterized by a glucid spectrum corresponding to:
   a content of monosaccharides (DP=1) less than 14%,
   a content of disaccharides (DP=2) less than 35%,
   a content of oligosaccharides of DP 4 to DP 10 ranging from 42% to 70%,
   a content of polysaccharides of DP higher than 10 less than 32%, and
   a content less than 3% of polyols of DP higher than 20.

2. Hydrogenated starch hydrolysate according to claim 1, wherein the content in products of DP 4 to DP 10 ranges from 42% to about 55% and the content in products of DP1 is less than about 5%.

3. Hydrogenated starch hydrolysate according to claim 1, wherein the content in products of DP 4 to DP 10 ranges from 42 to about 50% and the content in products of DP 1 is about 5% to 14%.

4. Hydrogenated starch hydrolysate according to claim 1, wherein the content in products of DP 4 to DP 10 ranges from 55% to 70%.

5. Pulverulent hydrogenated starch hydrolysate produced by spraying a hydrolysate according to claim 1.

6. Hydrogenated starch hydrolysate according to claim 1, wherein the content of disaccharides is less than 20%.

7. Hydrogenated starch hydrolysate according to claim 1, wherein the oligosaccharides of DP 5 to DP 7 represent by themselves a proportion higher than 25%.

8. Hydrogenated starch hydrolysate according to claim 1, wherein the oligosaccharides of DP 5 to DP 7 represent by themselves a proportion higher than 30%.

9. Hydrogenated starch hydrolysate according to claim 1, wherein the content of polysaccharides of DP higher than 10 is less than 25%.

10. Hydrogenated starch hydrolysate according to claim 1, wherein the content of polyols of DP higher than 20 is less than 1.5%.

11. Hydrogenated starch hydrolysate according to claim 1, wherein:
    the content of monosaccharides (DP=1) is less than 14%,
    the content of disaccharides (DP=2) is less than 20%,
    the content of oligosaccharides of DP 4 to DP 10 ranges from 42% to 60%, the oligosaccharides of DP 5 to DP 7 representing by themselves a proportion higher than 30%,
    the content of polysaccharides of DP higher than 10 is less than 25%, and
    the content of polyols of DP higher than 2 is less than 1.5%.

12. Hydrogenated starch hydrolysate according to claim 1, wherein the content of oligosaccharides of DP 4 to DP 10 ranges from 42% to 60%.

13. Hydrogenated starch hydrolysate according to claim 12, wherein the oligosaccharides of DP 5 to DP 7 represent by themselves a proportion higher than 25%.

14. Hydrogenated starch hydrolysate according to claim 12, wherein the oligosaccharides of DP 5 to DP 7 represent by themselves a proportion higher than 30%.

* * * * *